United States Patent [19]
Klein

[11] Patent Number: 5,028,144
[45] Date of Patent: Jul. 2, 1991

[54] BRAKE FLUID TESTING DEVICE

[76] Inventor: Lawrence W. Klein, R.R. 1, Box 20A, Alhambra, Ill. 62001

[21] Appl. No.: 391,148

[22] Filed: Aug. 8, 1989

[51] Int. Cl.$^5$ .................. B60Q 9/00; G01N 27/18
[52] U.S. Cl. .................. 374/44; 73/61.1 R; 73/73; 324/694; 324/698; 340/438; 374/10
[58] Field of Search .............. 73/61.1 R, 39, 121, 73/73; 340/631, 661; 324/698, 439, 705; 374/10

[56] References Cited

U.S. PATENT DOCUMENTS

| | | | |
|---|---|---|---|
| 2,552,088 | 5/1951 | Davis | 340/631 X |
| 2,752,566 | 6/1956 | Quinton | 324/698 |
| 2,977,797 | 4/1961 | Hoffmann et al. | 73/304 R |
| 4,074,226 | 2/1978 | Takada et al. | 340/453 X |
| 4,316,185 | 2/1982 | Watrous et al. | 340/661 X |
| 4,566,805 | 1/1986 | Klein et al. | 374/16 |
| 4,575,711 | 3/1986 | Suzuki et al. | 340/661 X |
| 4,654,645 | 3/1987 | Yamagishi | 324/698 X |
| 4,733,556 | 3/1988 | Meitzler et al. | 340/651 |
| 4,872,316 | 10/1989 | Browne et al. | 340/631 X |

Primary Examiner—Daniel M. Yasich
Attorney, Agent, or Firm—Armstrong, Teasdale, Schlafly, Davis & Dicus

[57] ABSTRACT

A brake fluid tester for measuring the quality of brake fluid, comprising means for measuring the conductivity of the brake fluid, preferably comprising a plurality of comparators for comparing the resistance of the brake fluid to a plurality of reference, resistances. The device further comprises indicating means, preferably light emitting diodes, responsive to the measuring means for indicating the quality of the brake fluid based upon its measured conductivity. An increasing number of diodes are illuminated as the conductivity of the brake fluid increases, providing a positive indication when the device is working and providing an easy to interpret display of the test results. The diodes are preferably activated at preselected levels of conductivity, corresponding to preselected levels of moisture contamination.

23 Claims, 1 Drawing Sheet

BRAKE FLUID TESTING DEVICE

BACKGROUND OF THE INVENTION

This invention relates to a device for testing brake fluid, and in particular to a device for testing the quality of brake fluid by measuring the conductivity of the brake fluid.

Water and corrosion products contaminate brake fluids, adversely affecting their performance and reducing their boiling points. Brake fluids are generally hygroscopic, i.e., they readily absorb water, and thus they rapidly deteriorate when exposed to water. This is a problem even for fresh brake fluid if it is not properly sealed. It has been experimentally determined that one percent moisture will lower the boiling point as much as 25% and three percent moisture will lower the boiling point 50%. This decrease in boiling point means that heat generated during the operation of the brakes can cause the water to boil out of the brake fluid, forming steam that impairs the operation of the brakes.

The deterioration of brake fluid is usually not apparent from the appearance of the brake fluid. For this reason at least some automobile manufacturers recommend that the brake fluid be frequently changed. Prior testing equipment for brake fluid was complicated, time consuming, and expensive. One prior device for testing brake fluid is disclosed in Klein et al., U.S. Pat. No. 4,566,805. This device operates by monitoring the temperature of a small heating element immersed in the fluid as the element is heated. The temperature of the element levels off briefly at the boiling point of the fluid, indicating the moisture content of the fluid.

SUMMARY OF THE INVENTION

It is among the objects of the present invention to provide a device for testing the quality of brake fluid, and in particular to provide such a device that tests the quality of brake fluid by measuring its conductivity or resistance and comparing it to preselected benchmarks. It is also among the objects of the present invention to provide such a device that measures the conductivity by comparing it to a reference. It is also among the objects of the present invention to provide such a device that is of simple and inexpensive construction; to provide such a device that provides a positive indication of both satisfactory and unsatisfactory quality to reduce the uncertainty of the test results, and to provide such a device that is easy to use encourage frequent use.

The brake fluid testing device of the present invention is adapted to measure the quality of brake fluid by measuring its conductivity. The conductivity of the brake fluid increases as the content of contaminants, for example water, increases. Generally, the testing device of the present invention comprises measuring means for measuring the conductivity of the brake fluid, and indicating means responsive to the measuring means for indicating the quality of the brake fluid based upon its measured conductivity.

The indicating means preferably comprises a plurality of actuable signal devices and means for actuating an increasing number of the actuable signal devices as the measured conductivitY reaches predetermined values corresponding to predetermined moisture contents. There are preferably four such signal devices, for example, light emitting diodes. The first of these diodes is illuminated at a nominal conductivity level to provide a positive indication that the device is operational and that fluid quality is satisfactory. The other diodes are lit for example at conductivities corresponding to 1 percent, two percent, and three percent moisture content in the fluid.

The device thus provides a way of testing the quality of brake fluid by measuring its conductivity and comparing it to preselected benchmarks. The device is of simple and inexpensive construction, and can be made to be hand held for easy use. The device provides a positive indication of both satisfactory and unsatisfactory quality to reduce the uncertainty of the test results, and does not require special training or instruction to use it.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
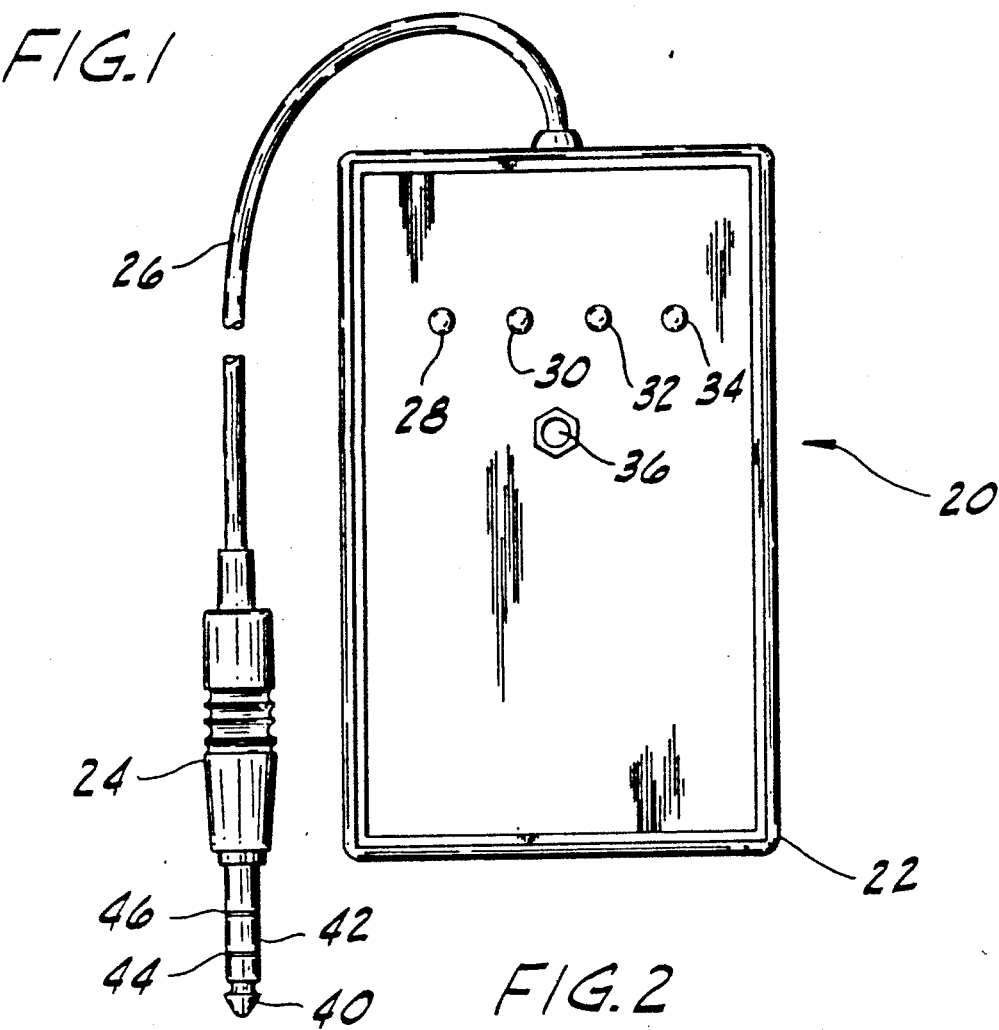
FIG. 1 is a plan view of a brake fluid testing device constructed according to the principles of this invention.

A brake fluid testing device constructed according to the principles of this invention is indicated generally as 20 in FIG. 1. The device is adapted to test the quality of brake fluid by measuring its conductivity or resistance. As used throughout conductivity and resistance are used interchangably. In fact, the preferred embodiment of this invention described herein measures the conductivity of brake fluid by comparing it to reference resistances. The device 20 comprises a case 22 and a test probe 24 connected to the case 22 with a coaxial cord 26.

The case 22 has four actuable signal devices, namely light emitting diodes 28, 30, 32 and 34. In this preferred embodiment diode 28 is green, diode 30 is amber, diode 32 is orange, and diode 34 is red, although the diodes could be some other color or the diodes could all be the same color. The case also has a push button momentary switch 36 for actuating the testing device, as described below.

Figure 2:
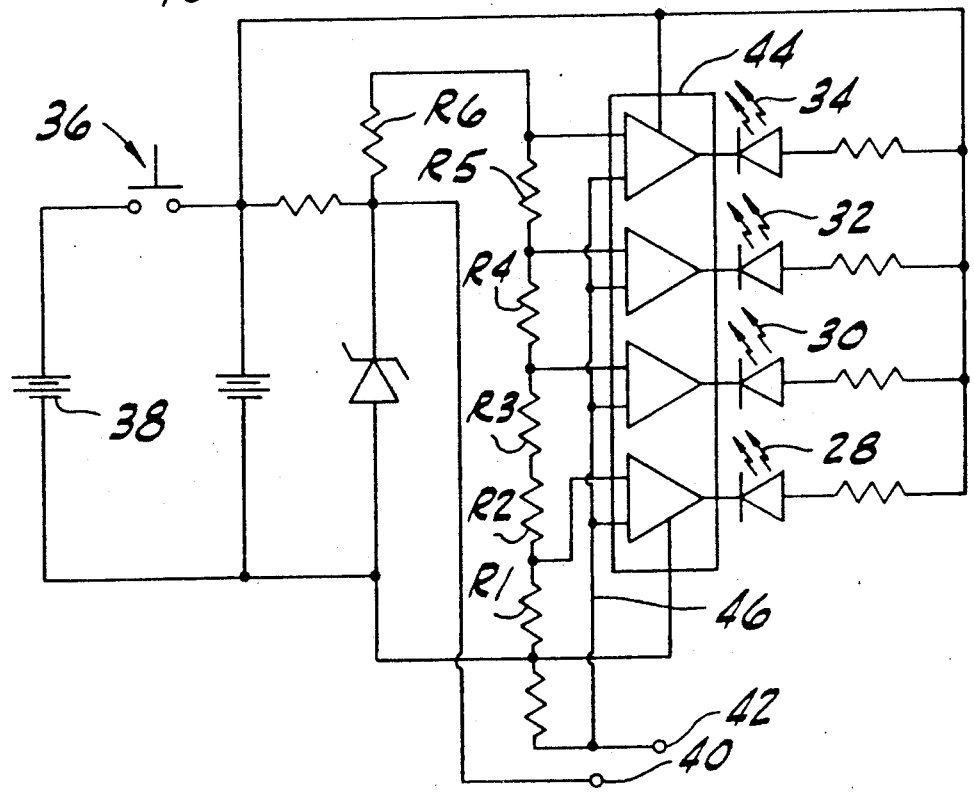
FIG. 2 is a schematic diagram of the electronic circuitry incorporated into the preferred embodiment of the brake fluid testing device.

The case 22 contains a circuit on a printed circuit board, which is shown schematically in FIG. 2. The case 22 also includes a compartment (not shown) for containing a battery 38 for powering the testing device. This battery 38 is preferably a standard 9 v battery.

The test probe 24 comprises two contacts 40 and 42, electrically separated from each other by an insulator 44, and electrically separated from the rest of the probe by an insulator 46. The circuit 38 is preferably tuned to the size and shape of the contacts 40 and 42, which affects the conductivity measured between the contacts. One of the two leads of coaxial cord 26 connects each of the contacts 40 and 42 to the circuit.

The circuit compares the conductivity (or resistance) between the contacts 40 and 42 with predetermined bench mark conductivities established by resistors R1-R6 in the circuit. These benchmark conductivities have been empirically determined to correspond with preselected moisture content levels. In this preferred embodiment the conductivities correspond to the conductivity of an average brake fluid with just slightly greater than about 0% moisture; the conductivity of an average brake fluid with about 1% moisture; the conductivity of an average brake fluid with about 2% moisture; and the conductivity of an average brake fluid with about 3% moisture. The inventor has empirically determined that for most brands of brake fluid, the benchmark values of conductivity and its equivalent resistance are as follows:

| CONDUCTIVITY | RESISTANCE | MOISTURE CONTENT |
| --- | --- | --- |
| $4.5 \times 10^{-6}$ mho | 221.06 K ohm | 0+% |
| $2.09 \times 10^{-5}$ mho | 47.66 K ohm | ~1% |
| $2.22 \times 10^{-5}$ mho | 44.92 K ohm | ~2% |
| $2.46 \times 10^{-5}$ mho | 40.54 K ohm | ~3% |

Of course the measured conductivity between the contacts 40 and 42 depends on the size and shape of the contacts. With a different probe the measured conductivity may vary somewhat, but the device is easily calibrated by adjusting the resistances in the circuit to correspond with the measured resistances between the contacts for selected moisture levels.

Reference character 44, illustrates an integrated circuit (IC) comprising a plurality of voltage comparators (four are illustrated) for comparing the resistance across terminals 40 and 42 to the resistors R1–R6. For example, IC 44 may be an SM8912 or LM399N manufactured by Motorolla, National Semiconductor, or Texas Instruments. As the resistance across terminals 40 and 42 decreases, the voltage applied to line 46 changes to trip one or more of the comparators which, in turn, energizes its associated LED.

In this preferred embodiment, when the measured resistance between the contacts 40 and 42 is about 221.06K ohm or less, the circuit causes the diode 28 (the green diode) to light up. This provides a positive indication that the device is operational and that the quality of the brake fluid is satisfactory. When the measured resistance is about 47.66K ohm or less, the circuit causes both the diode 28 and the diode 30 (the amber diode) to light up. When the measured resistance is about 44.92K ohm or less, the circuit causes the diodes 28, 30, and 32 (the orange diode) to light up. When the measured resistance is no more than about 40.54K ohm, the circuit causes all the diodes 28, 30, 32, and 34 (the red diode) to light up.

Thus the device provides different, readily understood signals as the moisture content of the brake fluid increases.

OPERATION

In operation, the probe 26 is immersed into the fluid to be tested, so that the contacts 40 and 42 are completely immersed in the fluid. The probe 26 can be inserted into the master cylinder of the brake system, if it is being used to test brake fluid in an operating brake system, or it can be inserted into a container of brake fluid, if it is being used to test the condition of brake fluid before it is put in a brake system.

The push button 36 is pressed and the circuit causes the appropriate number of diodes to light up. If the conductivity is extremely low, corresponding to a very low moisture content, only the green diode 28 lights up. This serves as a positive indication that the device is operational, and confirms that the quality of the brake fluid is satisfactory. If the moisture content is about 1%, diodes 28 and 30 light up. If the moisture content is about 2%, diodes 28, 30, and 32 light up. If the moisture content is at least about 3%, all of the diodes 28, 30, 32, and 34 light up. The increasing number of diodes gives a readily understood indication of the condition of the brake fluid, i.e., the moisture content and thus its boiling point. The more diodes that are lit, the more contaminated the fluid is, and thus the lower its boiling point. Furthermore, the color coding of the diodes further reinforces the meaning, the single green diode indicating satisfactory quality and the diodes ranging from amber, orange, to red representing deteriorating quality.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A brake fluid testing device for measuring the quality of brake fluid, the device comprising:
   measuring means for measuring the conductivity of the brake fluid; and
   indicating means responsive to the measuring means for indicating the quality of the brake fluid based on its measured conductivity, the indicating means comprising a plurality of actuable signal means and means for actuating each of the signal devices according to the relationship between the measured conductivity of the brake fluid and preselected benchmark values of the conductivity of the brake fluid being tested with preselected moisture contents.

2. The device according to claim 1 wherein the measuring means comprises means for comparing the conductivity to a reference.

3. The device according to claim 1 wherein the conductivity measuring means comprises means for measuring the resistance of the brake fluid.

4. The device according to claim 1 wherein the actuable signal devices comprise a plurality of light emitting diodes.

5. The device according to claim 1 wherein the benchmark values are selected to correspond to empirically determined conductivities of brake fluid with preselected moisture contents.

6. The device according to claim 5 where the means for actuating the signal devices actuates at least one actuable signal device when the measured conductivity is nominal, to indicate that the device is operational.

7. The device according to claim 1 wherein the actuating means actuates an increasing number of the actuable signal devices as the measured conductivity of the brake fluid increases.

8. A brake fluid testing device for measuring the quality of brake fluid, the device comprising:
   measuring means for measuring the conductivity of the brake fluid; and
   indicating means responsive to the measuring means for indicating the quality of the brake fluid based upon its measured conductivity, the indicating means including at least four actuable signal devices, and means for actuating one or more of the signal devices according to the measured conductivity of the brake fluid, the actuating means actuating an increasing number of the actuable signal devices as the measured conductivity of the brake fluid increases, the actuating means comprising means for actuating a first one of the signal devices when conductivity corresponding to nominal moisture in the brake fluid is measured; means for actuating a second one of the signal devices when conductivity corresponding to at least 1% moisture in the brake fluid is measured; means for actuating a third one of the signal devices when conductivity corresponding to at least 2% moisture in the brake fluid is measured; and means for actuating a fourth one of the signal devices when conductivity corresponding to 3% moisture in the brake fluid is measured.

9. The device according to claim 8 wherein the actuable signal devices comprise light emitting diodes.

10. A brake fluid testing device for measuring the quality of brake fluid, the device comprising:
measuring means for measuring the conductivity of the brake fluid;
indicating means responsive to the measuring means for indicating the quality of the brake fluid based upon its measured conductivity, the indicating means including at least four actuable signal devices, and means for actuating one or more of the signal devices according to the measured conductivity of the brake fluid, the actuating means actuating an increasing number of the actuable signal devices as the measured conductivity of the brake fluid increases, the actuating means comprising means for actuating a first one of the signal devices when conductivity measured is nominally greater than 0; means for actuating a second one of the signal devices when the conductivity measured is at least about $2.09 \times 10^{-5}$ mho; means for actuating a third one of the signal devices when the conductivity measured is at least about $2.22 \times 10^{-5}$ mhol; and means for actuating a fourth one of the signal devices when the conductivity measured is at least about $2.46 \times 10^{-5}$ mho.

11. The device according to claim 10 wherein the actuable signal devices comprise light emitting diodes.

12. A brake fluid testing device for measuring the quality of brake fluid, the device comprising:
a plurality of actuable signal devices; and
comparing means for comparing the conductivity of the brake fluid to preselected references and for actuating each of the actuable signal devices when the conductivity of the brake fluid, as determined by the comparing means, exceeds a preselected benchmark value of conductivity corresponding to that signal device.

13. The device according to claim 12 wherein the comparing means for comparing the conductivity of the brake fluid to preselected references comprises means for comparing the resistance of the brake fluid to a plurality of reference resistances.

14. The device according to claim 12 wherein the means for actuating the actuable signal devices actuates an increasing number of signal devices as the measured conductivity of the brake fluid increases.

15. The device according to claim 14 wherein the means for actuating the actuable signal devices actuates an additional signal device for an increase in conductivity corresponding to a preselected increase in moisture content.

16. A brake fluid testing device for measuring the quality of brake fluid, the device comprising:
at least four actuable signal devices; and
comparing means for comparing the conductivity of the brake fluid to a reference and for actuating the actuable signal devices in response to the comparison, the means for comparing and actuating the signal devices comprising means for actuating a first one of the signal devices when the conductivity of the brake fluid is at least as great as a reference corresponding to nominal moisture in the brake fluid; means for actuating a second one of the signal devices when the conductivity of the brake fluid is at least as great as a reference corresponding to at least 1% moisture in the brake fluid; means for actuating a third one of the signal devices when the conductivity of the brake fluid is at least as great as a reference corresponding to at least 2% moisture in the brake fluid; and means for actuating a fourth one of the signal devices when the conductivity of the brake fluid is at least as great as a reference corresponding to at least 3% moisture in the brake fluid.

17. The device according to claim 16 wherein the actuable signal devices comprises light emitting diodes.

18. A brake fluid testing device for measuring the quality of brake fluid, the device comprising:
at least four actuable signal devices; and
comparing means for comparing the conductivity of the brake fluid to a reference and for actuating the actuable signal devices in response to the comparison, the means for comparing and actuating the signals devices comprising means for actuating a first one of the signal devices when the conductivity of the brake fluid is at least as great as a reference of 0; means for actuating a second one of the signal devices when the conductivity of the brake fluid is at least as great as a reference of about $2.09 \times 10^{-5}$ mho; means for actuating a third one of the signal devices when the conductivity of the brake fluid is at least as great as a reference of about $2.22 \times 10^{-5}$ mho; and means for actuating a fourth one of the signal devices when the conductivity of the brake fluid is at least as great as a reference of about $2.46 \times 10^{-5}$ mho.

19. The device according to claim 18 wherein the actuable signal devices comprises light emitting diodes.

20. A method of testing the quality of brake fluid comprising the steps of:
measuring the conductivity of the brake fluid;
displaying a representation of the quality of the brake fluid with a plurality of signal devices by actuating particular signal devices as the measured conductivity of the brake fluid reaches predetermined benchmark values corresponding to preselected moisture contents.

21. The method of testing the quality of brake fluid according to claim 20 wherein the step of measuring the conductivity of the brake fluid comprises the step of comparing the conductivity of the brake fluid to preselected references.

22. The method of testing the quality of brake fluid according to claim 20 wherein the preselected references are being tested at preselected moisture contents.

23. A method of testing the quality of brake fluid comprising the steps of: comparing the conductivity of the brake fluid to predetermined references, corresponding to the conductivity of the brake fluid being tested at preselected moisture contents; and
actuating an actuable signal device corresponding to each reference depending upon the results of the comparison.

* * * * *